(12) United States Patent
Elomari

(10) Patent No.: US 7,390,395 B2
(45) Date of Patent: Jun. 24, 2008

(54) HYDROCARBON CONVERSION USING MOLECULAR SIEVE SSZ-56

(76) Inventor: Saleh Elomari, 905 Antiquity Dr., Fairfield, CA (US) 94534

( * ) Notice: Subject to any disclaimer, the term of this patent is extended or adjusted under 35 U.S.C. 154(b) by 190 days.

(21) Appl. No.: 11/454,312

(22) Filed: Jun. 16, 2006

(65) Prior Publication Data

US 2007/0034549 A1 Feb. 15, 2007

Related U.S. Application Data

(60) Provisional application No. 60/694,029, filed on Jun. 23, 2005.

(51) Int. Cl.
*B01J 29/04* (2006.01)
*C10G 73/02* (2006.01)
*C10G 47/24* (2006.01)
*C10G 35/06* (2006.01)
*C10G 45/00* (2006.01)

(52) U.S. Cl. .................. 208/108; 208/27; 208/120.35; 208/139; 208/143; 502/62; 585/467; 585/475; 585/481; 585/535; 585/639; 585/664

(58) Field of Classification Search .............. 208/27, 208/108, 120.35, 139, 143; 502/62; 585/467, 585/475, 481, 535, 639, 664
See application file for complete search history.

(56) References Cited

U.S. PATENT DOCUMENTS

| | | | |
|---|---|---|---|
| 3,140,249 A | 7/1964 | Plank et al. | |
| 3,140,251 A | 7/1964 | Plank et al. | |
| 3,140,253 A | 7/1964 | Woodbury et al. | |
| 3,849,107 A | 11/1974 | Fischer | |
| 3,852,207 A | 12/1974 | Stangeland et al. | |
| 3,904,513 A | 9/1975 | Fischer et al. | |
| 3,960,978 A | 6/1976 | Givens et al. | |
| 4,086,408 A | 4/1978 | Karol et al. | |
| 4,157,294 A | 6/1979 | Iwao et al. | |
| 4,181,598 A | 1/1980 | Gillespie et al. | |
| 4,347,121 A | 8/1982 | Mayer et al. | |
| 4,376,722 A | 3/1983 | Chester et al. | |
| 4,377,497 A | 3/1983 | Chester et al. | |
| 4,446,243 A | 5/1984 | Chester et al. | |
| 4,526,942 A | 7/1985 | Chester et al. | |
| 4,734,537 A | 3/1988 | Devries et al. | |
| 4,739,311 A | 4/1988 | Yamamoto et al. | |
| 4,910,006 A | 3/1990 | Zones et al. | |
| 4,921,594 A | 5/1990 | Miller | |
| 4,962,261 A | 10/1990 | Abrevaya et al. | |
| 5,095,161 A | 3/1992 | Abrevaya et al. | |
| 5,105,044 A | 4/1992 | Han et al. | |
| 5,105,046 A | 4/1992 | Washecheck | |
| 5,149,421 A | 9/1992 | Miller | |
| 5,225,179 A | 7/1993 | Zones et al. | |
| 5,238,898 A | 8/1993 | Han et al. | |
| 5,316,753 A | 5/1994 | Nakagawa | |
| 5,321,185 A | 6/1994 | Van der Vaart | |
| 5,336,825 A | 8/1994 | Choudhary et al. | |
| 6,540,906 B1 * | 4/2003 | Elomari | 208/120.35 |
| 6,547,958 B1 * | 4/2003 | Elomari | 208/120.35 |
| 6,616,830 B2 * | 9/2003 | Elomari | 208/120.35 |
| 6,808,620 B2 * | 10/2004 | Elomari | 208/120.35 |
| 2006/0288690 A1 | 12/2006 | Elomari | |
| 2006/0292052 A1 | 12/2006 | Elomari | |
| 2006/0292071 A1 | 12/2006 | Elomari | |

OTHER PUBLICATIONS

B.C. Lippens and J.H. de Bohr, Studies on Pore Systems in Catalysts V. the T Method, 1965, 319-323, 4, from the Department of Chemical Technology, Technological University of Delft, The Netherlands.
Akira Saito, Henry C. Foley, Argon porosimetry of selected molecular sieves; experiments and examination of the adapted Horvath-Kawazoe model, Microporous Materials, 1995, 531-542, 3, Center of Catalytic Science and Technology, Department of Chemical Engineering, University of Delaware, Newark, DE 19716, USA.

\* cited by examiner

*Primary Examiner*—Glenn Caldarola
*Assistant Examiner*—Prem C. Singh
(74) *Attorney, Agent, or Firm*—Susan M. Abernathy; Richard J. Sheridan

(57) ABSTRACT

The present invention relates to new crystalline molecular sieve SSZ-56 prepared using a N,N-diethyl-2-methyldecahydroquinolinium cation as a structure directing agent, methods for synthesizing SSZ-56 and processes employing SSZ-56 in a catalyst.

68 Claims, No Drawings

HYDROCARBON CONVERSION USING MOLECULAR SIEVE SSZ-56

This application claims the benefit of U.S. Provisional Application Ser. No. 60/694,029, filed Jun. 23, 2005.

BACKGROUND OF THE INVENTION

1. Field of the Invention

The present invention relates to new crystalline molecular sieve SSZ-56, a method for preparing SSZ-56 using a N,N-diethyl-2-methyldecahydroquinolinium cation as a structure directing agent and the use of SSZ-56 in catalysts for, e.g., hydrocarbon conversion reactions.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

SUMMARY OF THE INVENTION

The present invention is directed to a family of crystalline molecular sieves with unique properties, referred to herein as "molecular sieve SSZ-56" or simply "SSZ-56". Preferably, SSZ-56 is in its silicate, aluminosilicate, titanosilicate, vanadosilicate or borosilicate form. The term "silicate" refers to a molecular sieve having a high mole ratio of silicon oxide relative to aluminum oxide, preferably a mole ratio greater than 100, including molecular sieves comprised entirely of silicon oxide. As used herein, the term "aluminosilicate" refers to a molecular sieve containing both aluminum oxide and silicon oxide and the term "borosilicate" refers to a molecular sieve containing oxides of both boron and silicon.

In accordance with the present invention there is provided a process for converting hydrocarbons comprising contacting a hydrocarbonaceous feed at hydrocarbon converting conditions with a catalyst comprising the molecular sieve of this invention. The molecular sieve may be predominantly in the hydrogen form. It may also be substantially free of acidity. The invention includes such a process wherein the molecular sieve has a mole ratio greater than about 15 of (1) silicon oxide to (2) an oxide selected from aluminum oxide, gallium oxide, iron oxide, boron oxide, titanium oxide, indium oxide and mixtures thereof, and has, after calcination, the X-ray diffraction lines of Table 2.

Further provided by the present invention is a hydrocracking process comprising contacting a hydrocarbon feedstock under hydrocracking conditions with a catalyst comprising the molecular sieve of this invention, preferably predominantly in the hydrogen form.

This invention also includes a dewaxing process comprising contacting a hydrocarbon feedstock under dewaxing conditions with a catalyst comprising the molecular sieve of this invention, preferably predominantly in the hydrogen form.

The present invention also includes a process for improving the viscosity index of a dewaxed product of waxy hydrocarbon feeds comprising contacting the waxy hydrocarbon feed under isomerization dewaxing conditions with a catalyst comprising the molecular sieve of this invention, preferably predominantly in the hydrogen form.

The present invention further includes a process for producing a $C_{20+}$ lube oil from a $C_{20+}$ olefin feed comprising isomerizing said olefin feed under isomerization conditions over a catalyst comprising the molecular sieve of this invention. The molecular sieve may be predominantly in the hydrogen form. The catalyst may contain at least one Group VIII metal.

In accordance with this invention, there is also provided a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15-3000 psi (0.103-20.7 MPa) with a catalyst comprising the molecular sieve of this invention, preferably predominantly in the hydrogen form. The catalyst may contain at least one Group VIII metal. The catalyst may be a layered catalyst comprising a first layer comprising the molecular sieve of this invention, and a second layer comprising an aluminosilicate zeolite which is more shape selective than the molecular sieve of said first layer. The first layer may contain at least one Group VIII metal.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. (204° C.) and at a pressure of from about 15 psig to about 3000 psig (0.103-20.7 Mpa gauge) in the presence of added hydrogen gas with a catalyst comprising the molecular sieve of this invention. The molecular sieve may be predominantly in the hydrogen form. The catalyst may contain at least one Group VIII metal.

Further included in this invention is a process for isomerization dewaxing a raffinate comprising contacting said raffinate in the presence of added hydrogen with a catalyst comprising the molecular sieve of this invention. The raffinate may be bright stock, and the molecular sieve may be predominantly in the hydrogen form. The catalyst may contain at least one Group VIII metal.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the molecular sieve of this invention made substantially free of acidity by neutralizing said molecular sieve with a basic metal. Also provided in this invention is such a process wherein the molecular sieve contains a Group VIII metal component.

Also provided by the present invention is a catalytic cracking process comprising contacting a hydrocarbon feedstock in a reaction zone under catalytic cracking conditions in the absence of added hydrogen with a catalyst comprising the molecular sieve of this invention, preferably predominantly in the hydrogen form. Also included in this invention is such a catalytic cracking process wherein the catalyst additionally comprises a large pore crystalline cracking component.

This invention further provides an isomerization process for isomerizing $C_4$ to $C_7$ hydrocarbons, comprising contacting a feed having normal and slightly branched $C_4$ to $C_7$ hydrocarbons under isomerizing conditions with a catalyst comprising the molecular sieve of this invention, preferably predominantly in the hydrogen form. The molecular sieve may be impregnated with at least one Group VIII metal, preferably platinum. The catalyst may be calcined in a steam/air mixture at an elevated temperature after impregnation of the Group VIII metal.

Also provided by the present invention is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the molecular sieve of this invention, preferably predominantly in the hydrogen form. The olefin may be a $C_2$ to $C_4$ olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, naphthalene, naphthalene derivatives, dimethylnaphthalene or mixtures thereof.

Further provided in accordance with this invention is a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the molecular sieve of this invention, preferably predominantly in the hydrogen form. The aromatic hydrocarbon and the polyalkyl aromatic hydrocarbon may be present in a molar ratio of from about 1:1 to about 25:1, respectively.

The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention is a process to convert paraffins to aromatics which comprises contacting paraffins under conditions which cause paraffins to convert to aromatics with a catalyst comprising the molecular sieve of this invention, said catalyst comprising gallium, zinc, or a compound of gallium or zinc.

In accordance with this invention there is also provided a process for isomerizing olefins comprising contacting said olefin under conditions which cause isomerization of the olefin with a catalyst comprising the molecular sieve of this invention.

Further provided in accordance with this invention is a process for isomerizing an isomerization feed comprising an aromatic $C_8$ stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the molecular sieve of this invention.

The present invention further provides a process for oligomerizing olefins comprising contacting an olefin feed under oligomerization conditions with a catalyst comprising the molecular sieve of this invention.

This invention also provides a process for converting oxygenated hydrocarbons comprising contacting said oxygenated hydrocarbon with a catalyst comprising the molecular sieve of this invention under conditions to produce liquid products. The oxygenated hydrocarbon may be a lower alcohol.

Further provided in accordance with the present invention is a process for the production of higher molecular weight hydrocarbons from lower molecular weight hydrocarbons comprising the steps of:

(a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and (b) withdrawing from said reaction zone a higher molecular weight hydrocarbon-containing stream.

Also provided in accordance with this invention is a catalyst composition for promoting polymerization of 1-olefins, said composition comprising (A) a molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table 2; and (B) an organotitanium or organochromium compound.

Oxide (1) may be silicon oxide, and oxide (2) may be an oxide selected from aluminum oxide, gallium oxide, iron oxide, boron oxide, titanium oxide, indium oxide.

The present invention further provides a for polymerizing 1-olefins, which process comprises contacting 1-olefin monomer with a catalytically effective amount of a catalyst composition comprising (A) a molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table 2; and (B) an organotitanium or organochromium compound under polymerization conditions which include a temperature and pressure suitable for initiating and promoting the polymerization reaction.

Oxide (1) may be silicon oxide, and oxide (2) may be an oxide selected from aluminum oxide, gallium oxide, iron oxide, boron oxide, titanium oxide, indium oxide.

The present invention further provides a process for hydrogenating a hydrocarbon feed containing unsaturated hydrocarbons, the process comprising contacting the feed and hydrogen under conditions which cause hydrogenation with a catalyst comprising the molecular sieve of this invention. The catalyst can also contain metals, salts or complexes wherein the metal is selected from the group consisting of platinum, palladium, rhodium, iridium or combinations thereof, or the group consisting of nickel, molybdenum, cobalt, tungsten, titanium, chromium, vanadium, rhenium, manganese and combinations thereof.

In accordance with this invention, there is also provided a process for hydrotreating a hydrocarbon feedstock comprising contacting the feedstock with a hydrotreating catalyst and hydrogen under hydrotreating conditions, wherein the catalyst comprises the molecular sieve of this invention.

DETAILED DESCRIPTION OF THE INVENTION

The present invention comprises a family of crystalline molecular sieves designated herein "molecular sieve SSZ-56" or simply "SSZ-56". In preparing SSZ-56, a N,N-diethyl- 2-methyldecahydroquinolinium cation (the trans-fused ring isomer) is used as a structure directing agent ("SDA"), also known as a crystallization template. The SDA useful for making SSZ-56 has the following structure:

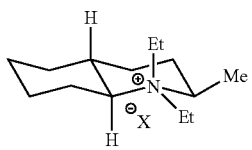

The SDA cation is associated with an anion (X$^-$) which may be any anion that is not detrimental to the formation of the molecular sieve. Representative anions include halogen, e.g., fluoride, chloride, bromide and iodide, hydroxide, acetate, sulfate, tetrafluoroborate, carboxylate, and the like. Hydroxide is the most preferred anion.

SSZ-56 is prepared from a reaction mixture having the composition shown in Table A below.

TABLE A

| | Reaction Mixture | |
| --- | --- | --- |
| | Typical | Preferred |
| $YO_2/W_aO_b$ | ≧15 | 30-60 |
| $OH^-/YO_2$ | 0.10-0.50 | 0.20-0.30 |
| $Q/YO_2$ | 0.05-0.50 | 0.10-0.30 |
| $M_{2/n}/YO_2$ | 0-0.40 | 0.10-0.25 |
| $H_2O/YO_2$ | 20-80 | 30-45 | where Y is silicon; W is aluminum, gallium, iron, boron, titanium, indium, vanadium or mixtures thereof; a is 1 or 2, b is 2 when a is 1 (i.e., W is tetravalent); b is 3 when a is 2 (i.e., W is trivalent); M is an alkali metal cation, alkaline earth metal cation or mixtures thereof; n is the valence of M (i.e., 1 or 2); and Q is a trans-fused ring N,N-diethyl-2-methyldecahydroquinolinium cation;

In practice, SSZ-56 is prepared by a process comprising:
(a) preparing an aqueous solution containing sources of oxides capable of forming a crystalline molecular sieve and a trans-fused ring N,N-diethyl-2-methyldecahydroquinolinium cation having an anionic counterion which is not detrimental to the formation of SSZ-56;
(b) maintaining the aqueous solution under conditions sufficient to form crystals of SSZ-56; and
(c) recovering the crystals of SSZ-56.

Accordingly, SSZ-56 may comprise the crystalline material and the SDA in combination with metallic and nonmetallic oxides bonded in tetrahedral coordination through shared oxygen atoms to form a cross-linked three dimensional crystal structure.

Typical sources of silicon oxide include silicates, silica hydrogel, silicic acid, fumed silica, colloidal silica, tetraalkyl orthosilicates, and silica hydroxides. Boron can be added in forms corresponding to its silicon counterpart, such as boric acid.

A source zeolite reagent may provide a source of boron. In most cases, the source zeolite also provides a source of silica. The source zeolite in its deboronated form may also be used as a source of silica, with additional silicon added using, for example, the conventional sources listed above. Use of a source zeolite reagent for the present process is more completely described in U.S. Pat. No. 5,225,179, issued Jul. 6, 1993 to Nakagawa entitled "Method of Making Molecular Sieves", the disclosure of which is incorporated herein by reference.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The SDA may be used to provide hydroxide ion. Thus, it may be beneficial to ion exchange, for example, the halide to hydroxide ion, thereby reducing or eliminating the alkali metal hydroxide quantity required. The alkali metal cation or alkaline earth cation may be part of the as-synthesized crystalline oxide material, in order to balance valence electron charges therein.

The reaction mixture is maintained at an elevated temperature until the crystals of the SSZ-56 are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Preferably, the molecular sieve is prepared using mild stirring or agitation.

During the hydrothermal crystallization step, the SSZ-56 crystals can be allowed to nucleate spontaneously from the reaction mixture. The use of SSZ-56 crystals as seed material can be advantageous in decreasing the time necessary for complete crystallization to occur. In addition, seeding can lead to an increased purity of the product obtained by promoting the nucleation and/or formation of SSZ-56 over any undesired phases. When used as seeds, SSZ-56 crystals are added in an amount between 0.1 and 10% of the weight of first tetravalent element oxide, e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-56 crystals. The drying step can be performed at atmospheric pressure or under vacuum.

SSZ-56 as prepared has a mole ratio of silicon oxide to boron oxide greater than about 15; and has, after calcination, the X-ray diffraction lines of Table 2 below. SSZ-56 further has a composition, as synthesized (i.e., prior to removal of the SDA from the SSZ-56) and in the anhydrous state, in terms of mole ratios, shown in Table B below.

TABLE B

| As-Synthesized SSZ-56 | |
| --- | --- |
| $YO_2/W_cO_d$ | 15-infinity |
| $M_{2/n}/YO_2$ | 0-0.03 |
| $Q/YO_2$ | 0.02-0.05 | where Y, W, M, n, and Q are as defined above and c is 1 or 2; d is 2 when c is 1 (i.e., W is tetravalent) or d is 3 or 5 when c is 2 (i.e., d is 3 when W is trivalent or 5 when W is pentavalent).

SSZ-56 can be an all-silica. SSZ-56 is made as a borosilicate and then the boron can be removed, if desired, by treating the borosilicate SSZ-56 with acetic acid at elevated temperature (as described in Jones et al., *Chem. Mater.*, 2001, 13, 1041-1050) to produce an all-silica version of SSZ-56 (i.e., $YO_2/W_cO_d$ is ∞).

If desired, SSZ-56 can be made as a borosilicate and then the boron can be removed as described above and replaced with metal atoms by techniques known in the art. Aluminum, gallium, iron, titanium, vanadium and mixtures thereof can be added in this manner.

It is believed that SSZ-56 is comprised of a new framework structure or topology which is characterized by its X-ray diffraction pattern. SSZ-56, as-synthesized, has a crystalline structure whose X-ray powder diffraction pattern exhibit the characteristic lines shown in Table 1 and is thereby distinguished from other molecular sieves.

TABLE 1

X-ray data for the as-synthesized Boron-SSZ-56

| 2θ[a] | d | Relative Intensity[b] |
|---|---|---|
| 6.58 | 13.43 | M |
| 7.43 | 11.88 | M |
| 7.93 | 11.14 | S |
| 8.41 | 10.51 | M |
| 13.22 | 6.69 | M |
| 13.93 | 5.95 | M |
| 14.86 | 5.95 | M |
| 22.59 | 3.93 | VS |
| 23.26 | 3.82 | VS |
| 24.03 | 3.70 | S |

[a]±0.10
[b]The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table 1A below shows the X-ray powder diffraction lines for as-synthesized SSZ-56 including actual relative intensities.

TABLE 1A

As-Synthesized SSZ-56

| 2θ[a] | d | I/Io × 100 Relative Intensity |
|---|---|---|
| 6.58 | 13.42 | 36.3 |
| 7.43 | 11.88 | 25.2 |
| 7.93 | 11.14 | 58.5 |
| 8.41 | 10.51 | 30.9 |
| 8.84 | 10.00 | 18.0 |
| 9.5 | 9.30 | 4.9 |
| 11.04 | 8.00 | 11.1 |
| 11.29 | 7.83 | 4.5 |
| 11.56 | 7.64 | 12.6 |
| 12.15 | 7.27 | 18.7 |
| 13.22 | 6.70 | 34.3 |
| 13.93 | 6.35 | 21.6 |
| 14.86 | 5.96 | 20.4 |
| 15.94 | 5.56 | 5.7 |
| 17.02 | 5.20 | 10.8 |
| 17.45 | 5.07 | 8.2 |
| 17.77 | 4.99 | 5.8 |
| 18.04 | 4.91 | 13.6 |
| 18.79 | 4.72 | 8.4 |
| 19.72 | 4.50 | 2.1 |
| 19.90 | 4.46 | 2.2 |
| 20.11 | 4.41 | 4.4 |
| 20.42 | 4.35 | 8.8 |
| 21.22 | 4.18 | 19.8 |
| 21.57 | 4.12 | 3.2 |
| 22.58 | 3.93 | 73.1 |
| 23.26 | 3.82 | 100.0 |
| 24.03 | 3.70 | 48.9 |
| 25.04 | 3.55 | 5.7 |
| 25.32 | 3.51 | 4.1 |
| 25.49 | 3.49 | 3.5 |
| 25.99 | 3.42 | 12.9 |
| 26.58 | 3.35 | 10.2 |
| 26.86 | 3.32 | 7.2 |
| 28.33 | 3.15 | 6.6 |
| 28.86 | 3.09 | 13.3 |
| 29.41 | 3.03 | 3.5 |
| 29.68 | 3.00 | 5.1 |
| 30.07 | 2.97 | 9.4 |
| 31.07 | 2.88 | 2.2 |
| 32.08 | 2.79 | 5.9 |
| 32.82 | 2.73 | 2.7 |
| 34.13 | 2.62 | 4.9 |
| 34.97 | 2.56 | 3.4 |
| 37.49 | 2.39 | 2.9 |

[a]±0.10

After calcination, the SSZ-56 molecular sieves have a crystalline structure whose X-ray powder diffraction pattern include the characteristic lines shown in Table 2:

TABLE 2

X-ray data for calcined SSZ-56

| 2θ | d | Relative Intensity |
|---|---|---|
| 6.54 | 13.51 | VS |
| 7.36 | 11.97 | VS |
| 7.89 | 11.20 | VS |
| 8.35 | 10.58 | VS |
| 8.81 | 10.03 | S |
| 13.16 | 6.72 | M |
| 14.83 | 5.96 | M |
| 22.48 | 3.95 | VS |
| 23.24 | 3.82 | VS |
| 23.99 | 3.70 | S |

[a]±0.10

Table 2A below shows the X-ray powder diffraction lines for calcined SSZ-56 including actual relative intensities.

TABLE 2A

Calcined SSZ-56

| 2θ[a] | d | I/Io × 100 Relative Intensity |
|---|---|---|
| 6.54 | 13.51 | 70.0 |
| 7.38 | 11.97 | 69.3 |
| 7.89 | 11.20 | 85.2 |
| 8.35 | 10.58 | 68.7 |
| 8.81 | 10.03 | 43.2 |
| 11.23 | 7.87 | 14.7 |
| 11.52 | 7.68 | 5.6 |
| 12.09 | 7.31 | 9.9 |
| 13.16 | 6.72 | 23.3 |
| 13.89 | 6.37 | 11.1 |
| 14.42 | 6.14 | 9.3 |
| 14.83 | 5.97 | 38.5 |
| 15.89 | 5.57 | 8.1 |
| 16.95 | 5.22 | 6.0 |
| 17.41 | 5.09 | 5.4 |
| 17.75 | 5.00 | 6.7 |
| 17.96 | 4.93 | 6.3 |
| 18.75 | 4.73 | 7.7 |
| 19.05 | 4.66 | 3.3 |
| 20.00 | 4.44 | 7.5 |
| 20.36 | 4.36 | 5.0 |
| 21.15 | 4.19 | 16.9 |
| 21.55 | 4.12 | 4.5 |

TABLE 2A-continued

Calcined SSZ-56

| 2θ[a] | d | I/Io × 100 Relative Intensity |
|---|---|---|
| 22.48 | 3.95 | 63.0 |
| 23.24 | 3.82 | 100.0 |
| 23.99 | 3.71 | 44.8 |
| 25.15 | 3.54 | 4.4 |
| 25.41 | 3.50 | 2.6 |
| 25.96 | 3.43 | 15.6 |
| 26.51 | 3.36 | 10.2 |
| 26.83 | 3.32 | 6.5 |
| 28.19 | 3.16 | 10.6 |
| 28.80 | 3.10 | 15.7 |
| 29.28 | 3.05 | 2.7 |
| 30.02 | 2.97 | 11.3 |
| 30.98 | 2.88 | 3.0 |
| 31.99 | 2.80 | 5.5 |
| 32.72 | 2.73 | 4.3 |
| 34.04 | 2.63 | 5.9 |
| 34.42 | 2.60 | 2.6 |
| 34.70 | 2.58 | 4.1 |
| 35.34 | 2.54 | 2.1 |
| 36.05 | 2.49 | 2.7 |
| 37.41 | 2.40 | 2.8 |
| 39.76 | 2.26 | 1.8 |

[a] ±0.10

The X-ray powder diffraction patterns were determined by standard techniques: The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.10 degrees.

The X-ray diffraction pattern of Table 1 is representative of "as-synthesized" or "as-made" SSZ-56 molecular sieves. Minor variations in the diffraction pattern can result from variations in the silica-to-boron mole ratio of the particular sample due to changes in lattice constants. In addition, sufficiently small crystals will affect the shape and intensity of peaks, leading to significant peak broadening.

Representative peaks from the X-ray diffraction pattern of calcined SSZ-56 are shown in Table 2. Calcination can also result in changes in the intensities of the peaks as compared to patterns of the "as-made" material, as well as minor shifts in the diffraction pattern. The molecular sieve produced by exchanging the metal or other cations present in the molecular sieve with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline SSZ-56 can be used as-synthesized, but preferably will be thermally treated (calcined). Usually, it is desirable to remove the alkali metal cation by ion exchange and replace it with hydrogen, ammonium, or any desired metal ion. The molecular sieve can be leached with chelating agents, e.g., EDTA or dilute acid solutions, to increase the silica to alumina mole ratio. The molecular sieve can also be steamed; steaming helps stabilize the crystalline lattice to attack from acids.

The molecular sieve can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired.

Metals may also be introduced into the molecular sieve by replacing some of the cations in the molecular sieve with metal cations via standard ion exchange techniques (see, for example, U.S. Pat. Nos. 3,140,249 issued Jul. 7, 1964 to Plank et al.; 3,140,251 issued Jul. 7, 1964 to Plank et al.; and 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-56. The SSZ-56 can also be impregnated with the metals, or the metals can be physically and intimately admixed with the SSZ-56 using standard methods known to the art.

Typical ion-exchange techniques involve contacting the synthetic molecular sieve with a solution containing a salt of the desired replacing cation or cations. Although a wide variety of salts can be employed, chlorides and other halides, acetates, nitrates, and sulfates are particularly preferred. The molecular sieve is usually calcined prior to the ion-exchange procedure to remove the organic matter present in the channels and on the surface, since this results in a more effective ion exchange. Representative ion exchange techniques are disclosed in a wide variety of patents including U.S. Pat. Nos. 3,140,249 issued on Jul. 7, 1964 to Plank et al.; 3,140,251 issued on Jul. 7, 1964 to Plank et al.; and 3,140,253 issued on Jul. 7, 1964 to Plank et al.

Following contact with the salt solution of the desired replacing cation, the molecular sieve is typically washed with water and dried at temperatures ranging from 65° C. to about 200° C. After washing, the molecular sieve can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-56, the spatial arrangement of the atoms which form the basic crystal lattice of the molecular sieve remains essentially unchanged.

SSZ-56 can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the SSZ-56 can be extruded before drying, or, dried or partially dried and then extruded.

SSZ-56 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

SSZ-56 zeolites are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-56 are expected to be useful include hydrocracking, dewaxing, catalytic cracking and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, polymerization of 1-olefins (e.g., ethylene), reforming, isomerizing polyalkyl substituted aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives, and forming higher molecular weight hydrocarbons from lower molecular weight hydrocarbons (e.g., methane upgrading).

The SSZ-56 catalysts may have high selectivity, and under hydrocarbon conversion conditions can provide a high percentage of desired products relative to total products.

For high catalytic activity, the SSZ-56 zeolite should be predominantly in its hydrogen ion form. Generally, the zeolite is converted to its hydrogen form by ammonium exchange followed by calcination. If the zeolite is synthesized with a high enough ratio of SDA cation to sodium ion, calcination alone may be sufficient. It is preferred that, after calcination, at least 80% of the cation sites are occupied by hydrogen ions and/or rare earth ions. As used herein, "predominantly in the hydrogen form" means that, after calcination, at least 80% of the cation sites are occupied by hydrogen ions and/or rare earth ions.

SSZ-56 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising SSZ-56 in the hydrocarbon conversion reactions of this invention. Preferred conditions are indicated in parentheses.

| Process | Temp., °C. | Pressure | LHSV |
|---|---|---|---|
| Hydrocracking | 175-485 | 0.5-350 bar | 0.1-30 |
| Dewaxing | 200-475 (250-450) | 15-3000 psig, 0.103-20.7 Mpa gauge (200-3000, 1.38-20.7 Mpa gauge) | 0.1-20 (0.2-10) |
| Aromatics formation | 400-600 (480-550) | atm.-10 bar | 0.1-15 |
| Cat. Cracking | 127-885 | subatm.[1] (atm.-5 atm.) | 0.5-50 |
| Oligomerization | 232-649[2] 10-232[4] (27-204)[4] | 0.1-50 atm.[2,3] — — | 0.2-50[2] 0.05-20[5] (0.1-10)[5] |
| Paraffins to aromatics | 100-700 | 0-1000 psig | 0.5-40[5] |
| Condensation of alcohols | 260-538 | 0.5-1000 psig, 0.00345-6.89 Mpa gauge | 0.5-50[5] |
| Isomerization | 93-538 (204-315) | 50-1000 psig, 0.345-6.89 Mpa gauge | 1-10 (1-4) |
| Xylene isomerization | 260-593[2] (315-566)[2] 38-371[4] | 0.5-50 atm.[2] (1-5 atm)[2] 1-200 atm.[4] | 0.1-100[5] (0.5-50)[5] 0.5-50 |

[1] Several hundred atmospheres
[2] Gas phase reaction
[3] Hydrocarbon partial pressure
[4] Liquid phase reaction
[5] WHSV Other reaction conditions and parameters are provided below.

Hydrocracking

Using a catalyst which comprises SSZ-56, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. No. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

SSZ-56, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with SSZ-56 under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 30,000 SCF/bbl (standard cubic feet per barrel) (0.089 to 5.34 SCM/liter (standard cubic meters/liter)), preferably about 1000 to about 20,000 SCF/bbl (0.178 to 3.56 SCM/liter). Generally, hydrogen will be separated from the product and recycled to the reaction zone. Typical feedstocks include light gas oil, heavy gas oils and reduced crudes boiling above about 350° F. (177° C.).

A typical dewaxing process is the catalytic dewaxing of a hydrocarbon oil feedstock boiling above about 350° F. (177° C.) and containing straight chain and slightly branched chain hydrocarbons by contacting the hydrocarbon oil feedstock in the presence of added hydrogen gas at a hydrogen pressure of about 15-3000 psi (0.103-20.7 Mpa) with a catalyst comprising SSZ-56 and at least one Group VIII metal.

The SSZ-56 hydrodewaxing catalyst may optionally contain a hydrogenation component of the type commonly employed in dewaxing catalysts. See the aforementioned U.S. Pat. No. 4,910,006 and U.S. Pat. No. 5,316,753 for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isomerization dewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

SSZ-56 may also be utilized as a dewaxing catalyst in the form of a layered catalyst. That is, the catalyst comprises a first layer comprising zeolite SSZ-56 and at least one Group VIII metal, and a second layer comprising an aluminosilicate zeolite which is more shape selective than zeolite SSZ-56. The use of layered catalysts is disclosed in U.S. Pat. No. 5,149,421, issued Sep. 22, 1992 to Miller, which is incorporated by reference herein in its entirety. The layering may also include a bed of SSZ-56 layered with a non-zeolitic component designed for either hydrocracking or hydrofinishing.

SSZ-56 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig (2.76 to 20.7 Mpa gauge) at space velocities (LHSV) between about 0.1 and 20 and a hydrogen recycle rate of about 400 to 1500 SCF/bbl (0.071 to 0.27 SCM/liter). The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using SSZ-56. For example, a $C_{20+}$ lube oil may be made by isomerizing a $C_{20+}$ olefin feed over a catalyst comprising SSZ-56 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. (204° C.) and at a pressure of from about 15 psig to about 3000 psig (0.103-20.7 Mpa gauge) in the presence of added hydrogen gas with a catalyst comprising SSZ-56 in the hydrogen form and at least one Group VIII metal.

Aromatics Formation

SSZ-56 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising SSZ-56. It is also possible to convert heavier feeds into BTX or naphthalene derivatives of value using a catalyst comprising SSZ-56.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the zeolite with a basic metal, e.g., alkali metal, compound. Methods for rendering the catalyst free of acidity are known in the art. See the aforementioned U.S. Pat. No. 4,910,006 and U.S. Pat. No. 5,316,753 for a description of such methods.

The preferred alkali metals are sodium, potassium, rubidium and cesium. The zeolite itself can be substantially free of acidity only at very high silica:alumina mole ratios.

Catalytic Cracking

Hydrocarbon cracking stocks can be catalytically cracked in the absence of hydrogen using SSZ-56, preferably predominantly in the hydrogen form.

When SSZ-56 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. No. 4,910,006 and U.S. Pat. No. 5,316,753. When a traditional cracking catalyst (TC) component is employed, the relative weight ratio of the TC to the SSZ-56 is generally between about 1:10 and about 500:1, desirably between about 1:10 and about 200:1, preferably between about 1:2 and about 50:1, and most preferably is between about 1:1 and about 20:1. The novel zeolite and/or the traditional cracking component may be further ion exchanged with rare earth ions to modify selectivity.

The cracking catalysts are typically employed with an inorganic oxide matrix component. See the aforementioned U.S. Pat. No. 4,910,006 and U.S. Pat. No. 5,316,753 for examples of such matrix components.

Isomerization

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst, i.e., a catalyst comprising SSZ-56 in the hydrogen form, with a hydrocarbon feed under isomerization conditions. The feed is preferably a light straight run fraction, boiling within the range of 30° F. to 250° F. (−1° C. to 121° C.) and preferably from 60° F. to 200° F. (16° C. to 93° C.). Preferably, the hydrocarbon feed for the process comprises a substantial amount of $C_4$ to $C_7$ normal and slightly branched low octane hydrocarbons, more preferably $C_5$ and $C_6$ hydrocarbons.

It is preferable to carry out the isomerization reaction in the presence of hydrogen. Preferably, hydrogen is added to give a hydrogen to hydrocarbon ratio ($H_2$/HC) of between 0.5 and 10$H_2$/HC, more preferably between 1 and 8$H_2$/HC. See the aforementioned U.S. Pat. No. 4,910,006 and U.S. Pat. No. 5,316,753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. No. 4,910,006 and U.S. Pat. No. 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. No. 4,910,006 and U.S. Pat. No. 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

SSZ-56 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising SSZ-56.

SSZ-56 can also be used for removing benzene from gasoline by alkylating the benzene as described above and removing the alkylated product from the gasoline.

For high catalytic activity, the SSZ-56 zeolite should be predominantly in its hydrogen ion form. It is preferred that, after calcination, at least 80% of the cation sites are occupied by hydrogen ions and/or rare earth ions.

Examples of suitable aromatic hydrocarbon feedstocks which may be alkylated or transalkylated by the process of the invention include aromatic compounds such as benzene, toluene and xylene. The preferred aromatic hydrocarbon is benzene. There may be occasions where naphthalene or naphthalene derivatives such as dimethylnaphthalene may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F. (38° C. to 315° C.), preferably 250° F. to 450° F. (121° C. to 232° C.). The reaction pressure should be sufficient to maintain at least a partial liquid phase in order to retard catalyst fouling. This is typically 50 psig to 1000 psig (0.345 to 6.89 Mpa gauge) depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F. (38° C. to 315° C.), but it is preferably about 250° F. to 450° F. (121° C. to 232° C.). The reaction pressure should be sufficient to maintain at least a partial liquid phase, typically in the range of about 50 psig to 1000 psig (0.345 to 6.89 Mpa gauge), preferably 300 psig to 600 psig (2.07 to 4.14 Mpa gauge). The weight hourly space velocity will range from about 0.1 to 10. U.S. Pat. No. 5,082,990 issued on Jan. 21, 1992 to Hsieh, et al. describes such processes and is incorporated herein by reference.

Conversion of Paraffins to Aromatics

SSZ-56 can be used to convert light gas $C_2$-$C_6$ paraffins to higher molecular weight hydrocarbons including aromatic compounds. Preferably, the zeolite will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Isomerization of Olefins

SSZ-56 can be used to isomerize olefins. The feed stream is a hydrocarbon stream containing at least one $C_{4-6}$ olefin, preferably a $C_{4-6}$ normal olefin, more preferably normal butene. Normal butene as used in this specification means all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40-60 weight percent normal butenes. A methyl-tert-butyl ether unit effluent typically contains 40-100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the SSZ-56. The process may be carried out generally at a temperature from about 625° F. to about 950° F. (329-510° C.), for butenes, preferably from about 700° F. to about 900° F. (371-482° C.), and about 350° F. to about 650° F. (177-343° C.) for pentenes and hexenes. The pressure ranges from subatmospheric to about 200 psig (1.38 Mpa gauge), preferably from about 15 psig to about 200 psig (0.103 to 1.38 Mpa gauge), and more preferably from about 1 psig to about 150 psig (0.00689 to 1.03 Mpa gauge).

The liquid hourly space velocity during contacting is generally from about 0.1 to about 50 $hr^{-1}$, based on the hydrocarbon feed, preferably from about 0.1 to about 20 $hr^{-1}$, more preferably from about 0.2 to about 10 $hr^{-1}$, most preferably from about 1 to about 5 $hr^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Xylene Isomerization

SSZ-56 may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt. % of a hydrogenation/dehydrogenation component selected from Group VIII (of the Periodic Table) metal component, especially platinum or nickel. By Group VIII metal component is meant the metals and their compounds such as oxides and sulfides.

Optionally, the isomerization feed may contain 10 to 90 wt. of a diluent such as toluene, trimethylbenzene, naphthenes or paraffins.

Oligomerization

It is expected that SSZ-56 can also be used to oligomerize straight and branched chain olefins having from about 2 to 21 and preferably 2-5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-56.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such zeolites may be obtained by steaming, by use in a conversion process or by any other method which may occur to one skilled in this art.

Condensation of Alcohols

SSZ-56 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Methane Upgrading

Higher molecular weight hydrocarbons can be formed from lower molecular weight hydrocarbons by contacting the lower molecular weight hydrocarbon with a catalyst comprising SSZ-56 and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide and or actinide metals or metal compounds.

These reactions, the metals or metal compounds employed and the conditions under which they can be run are disclosed in U.S. Pat. No. 4,734,537, issued Mar. 29, 1988 to Devries et al.; U.S. Pat. No. 4,939,311, issued Jul. 3, 1990 to Washecheck et al.; U.S. Pat. No. 4,962,261, issued Oct. 9, 1990 to Abrevaya et al.; U.S. Pat. No. 5,095,161, issued Mar. 10, 1992 to Abrevaya et al.; U.S. Pat. No. 5,105,044, issued Apr. 14, 1992 to Han et al.; U.S. Pat. No. 5,105,046, issued Apr. 14, 1992 to Washecheck; U.S. Pat. No. 5,238,898, issued Aug. 24, 1993 to Han et al.; U.S. Pat. No. 5,321,185, issued Jun. 14, 1994 to van der Vaart; and U.S. Pat. No. 5,336,825, issued Aug. 9, 1994 to Choudhary et al., each of which is incorporated herein by reference in its entirety.

Polymerization of 1-Olefins

The molecular sieve of the present invention may be used in a catalyst for the polymerization of 1-olefins, e.g., the polymerization of ethylene. To form the olefin polymerization catalyst, the molecular sieve as hereinbefore described is reacted with a particular type of organometallic compound. Organometallic compounds useful in forming the polymerization catalyst include trivalent and tetravalent organotitanium and organochromium compounds having alkyl moieties and, optionally, halo moieties. In the context of the present invention the term "alkyl" includes both straight and branched chain alkyl, cycloalkyl and alkaryl groups such as benzyl.

Examples of trivalent and tetravalent organochromium and organotitanium compounds are disclosed in U.S. Pat. No. 4,376,722, issued Mar. 15, 1983 to Chester et al., U.S. Pat. No. 4,377,497, issued Mar. 22, 1983 to Chester et al., U.S. Pat. No. 4,446,243, issued May 1, 1984 to Chester et al., and U.S. Pat. No. 4,526,942, issued Jul. 2, 1985 to Chester et al. The disclosure of the aforementioned patents are incorporated herein by reference in their entirety.

Examples of the organometallic compounds used to form the polymerization catalyst include, but are not limited to, compounds corresponding to the general formula:

$$MY_nX_{m-n}$$

wherein M is a metal selected from titanium and chromium; Y is alkyl; X is halogen (e.g., Cl or Br); n is 1-4; and m is greater than or equal to n and is 3 or 4.

Examples of organotitanium and organochromium compounds encompassed by such a formula include compounds of the formula $CrY_4$, $CrY_3$, $CrY_3X$, $CrY_2X$, $CrY_2X_2$, $CrYX_2$, $CrYX_3$, $TiY_4$, $TiY_3$, $TiY_3X$, $TiY_2X$, $TiY_2X_2$, $TiYX_2$, $TiYX_3$, wherein X can be Cl or Br and Y can be methyl, ethyl, propyl, isopropyl, butyl, isobutyl, sec-butyl, tert-butyl, pentyl, isopentyl, neopentyl, hexyl, isohexyl, neohexyl, 2-ethylbutyl, octyl, 2-ethylhexyl, 2,2-diethylbutyl, 2-isopropyl-3-methylbutyl, etc., cyclohexylalkyls such as, for example, cyclohexylmethyl, 2-cyclohexylethyl, 3-cyclyhexylpropyl, 4-cyclohexylbutyl, and the corresponding alkyl-substituted cyclohexyl radicals as, for example, (4-methylcyclohexyl) methyl, neophyl, i.e., beta, beta-dimethyl-phenethyl, benzyl, ethylbenzyl, and p-isopropylbenzyl. Preferred examples of Y include $C_{1-5}$ alkyl, especially butyl.

The organotitanium and organochromium materials employed in the catalyst can be prepared by techniques well known in the art. See, for example the aforementioned Chester et al. patents.

The organotitanium or organochromium compounds can be with the molecular sieve of the present invention, such as by reacting the organometallic compound and the molecular sieve, in order to form the olefin polymerization catalyst. Generally, such a reaction takes place in the same reaction medium used to prepare the organometallic compound under conditions which promote formation of such a reaction product. The molecular sieve can simply be added to the reaction mixture after formation of the organometallic compound has been completed. Molecular sieve is added in an amount sufficient to provide from about 0.1 to 10 parts by weight, preferably from about 0.5 to 5 parts by weight, of organometallic compound in the reaction medium per 100 parts by weight of molecular sieve.

Temperature of the reaction medium during reaction of organometallic compound with molecular sieve is also maintained at a level which is low enough to ensure the stability of the organometallic reactant. Thus, temperatures in the range of from about −150° C. to 50° C., preferably from about −80° C. to 0° C. can be usefully employed. Reaction times of from about 0.01 to 10 hours, more preferably from about 0.1 to 1 hour, can be employed in reacting the organotitanium or organochromium compound with the molecular sieve.

Upon completion of the reaction, the catalyst material so formed may be recovered and dried by evaporating the reaction medium solvent under a nitrogen atmosphere. Alternatively, olefin polymerization reactions can be conducted in this same solvent based reaction medium used to form the catalyst.

The polymerization catalyst can be used to catalyze polymerization of 1-olefins. The polymers produced using the catalysts of this invention are normally solid polymers of at least one mono-1-olefin containing from 2 to 8 carbon atoms per molecule. These polymers are normally solid homopolymers of ethylene or copolymers of ethylene with another mono-1-olefin containing 3 to 8 carbon atoms per molecule. Exemplary copolymers include those of ethylene/propylene, ethylene/1-butene, ethylene/1-hexane, and ethylene/1-octene and the like. The major portion of such copolymers is derived from ethylene and generally consists of about 80-99, preferably 95-99 mole percent of ethylene. These polymers are well suited for extrusion, blow molding, injection molding and the like.

The polymerization reaction can be conducted by contacting monomer or monomers, e.g., ethylene, alone or with one or more other olefins, and in the substantial absence of catalyst poisons such as moisture and air, with a catalytic amount of the supported organometallic catalyst at a temperature and at a pressure sufficient to initiate the polymerization reaction. If desired, an inert organic solvent may be used as a diluent and to facilitate materials handling if the polymerization reaction is conducted with the reactants in the liquid phase, e.g. in a particle form (slurry) or solution process. The reaction may also be conducted with reactants in the vapor phase, e.g., in a fluidized bed arrangement in the absence of a solvent but, if desired, in the presence of an inert gas such as nitrogen.

The polymerization reaction is carried out at temperatures of from about 30° C. or less, up to about 200° C. or more, depending to a great extent on the operating pressure, the pressure of the olefin monomers, and the particular catalyst being used and its concentration. Naturally, the selected operating temperature is also dependent upon the desired polymer melt index since temperature is definitely a factor in adjusting the molecular weight of the polymer. Preferably, the temperature used is from about 30° C. to about 100° C. in a conventional slurry or "particle forming" process or from 100° C. to 150° C. in a "solution forming" process. A temperature of from about 70° C. to 110° C. can be employed for fluidized bed processes.

The pressure to be used in the polymerization reactions can be any pressure sufficient to initiate the polymerization of the monomer(s) to high molecular weight polymer. The pressure, therefore, can range from subatmospheric pressures, using an inert gas as diluent, to superatmospheric pressures of up to about 30,000 psig or more. The preferred pressure is from atmospheric (0 psig) up to about 1000 psig. As a general rule, a pressure of 20 to 800 psig is most preferred.

The selection of an inert organic solvent medium to be employed in the solution or slurry process embodiments of this invention is not too critical, but the solvent should be inert to the supported organometallic catalyst and olefin polymer produced, and be stable at the reaction temperature used. It is not necessary, however, that the inert organic solvent medium also serve as a solvent for the polymer to be produced. Among the inert organic solvents applicable for such purposes may be mentioned saturated aliphatic hydrocarbons having from about 3 to 12 carbon atoms per molecule such as hexane, heptane, pentane, isooctane, purified kerosene and the like, saturated cycloaliphatic hydrocarbons having from about 5 to 12 carbon atoms per molecule such as cyclohexane, cyclopentane, dimethylcyclopentane and methylcyclohexane and the like and aromatic hydrocarbons having from about 6 to 12 carbon atoms per molecule such as benzene, toluene, xylene, and the like. Particularly preferred solvent media are cyclohexane, pentane, hexane and heptane.

Hydrogen can be introduced into the polymerization reaction zone in order to decrease the molecular weight of the polymers produced (i.e., give a much higher Melt Index, MI). Partial pressure of hydrogen when hydrogen is used can be within the range of 5 to 100 psig, preferably 25 to 75 psig. The melt indices of the polymers produced in accordance with the instant invention can range from about 0.1 to about 70 or even higher.

More detailed description of suitable polymerization conditions including examples of particle form, solution and fluidized bed polymerization arrangements are found in Karapinka; U.S. Pat. No. 3,709,853; Issued Jan. 9, 1973 and Karol et al; U.S. Pat. No. 4,086,408; Issued Apr. 25, 1978. Both of these patents are incorporated herein by reference.

Hydrotreating

SSZ-56 is useful in a hydrotreating catalyst. During hydrotreatment, oxygen, sulfur and nitrogen present in the hydrocarbonaceous feed is reduced to low levels. Aromatics and olefins, if present in the feed, may also have their double bonds saturated. In some cases, the hydrotreating catalyst and hydrotreating conditions are selected to minimize cracking reactions, which can reduce the yield of the most desulfided product (typically useful as a fuel).

Hydrotreating conditions typically include a reaction temperature between 400-900° F. (204-482° C.), preferably 650-850° F. (343-454° C.); a pressure between 500 and 5000 psig (3.5-34.6 Mpa), preferably 1000 to 3000 psig (7.0-20.8 MPa); a feed rate (LHSV) of 0.5 $hr^{-1}$ to 20 $hr^{-1}$ (v/v); and overall hydrogen consumption 300 to 2000 scf per barrel of liquid hydrocarbon feed (53.4-356 $m^3$ $H_2/m^3$ feed). The hydrotreating catalyst will typically be a composite of a Group VI metal or compound thereof, and a Group VIII metal or compound thereof supported on the molecular sieve of this invention. Typically, such hydrotreating catalyst are presulfided.

Catalysts useful for hydrotreating hydrocarbon feeds are disclosed in U.S. Pat. No. 4,347,121, issued Aug. 31, 1982 to Mayer et al, and U.S. Pat. No. 4,810,357, issued Mar. 7, 1989 to Chester et al, both of which are incorporated herein by reference in their entirety. Suitable catalysts include noble metals from Group VIII, such as Fe, Co, Ni, Pt or Pd, and/or Group VI metals, such as Cr, Mo, Sn or W. Examples of combinations of Group VIII and Group VI metals include Ni—Mo or Ni—Sn. Other suitable catalysts are described in U.S. Pat. No. 4,157,294, issued Jun. 5, 1979 to Iwao et al, and U.S. Pat. No. 3,904,513, issued Sep. 9, 1975 to Fischer et al. U.S. Pat. No. 3,852,207, issued Dec. 3, 1974 to Strangeland et al, describes suitable noble metal catalysts and mild hydrotreating conditions. The contents of these patents are hereby incorporated by reference.

The amount of hydrogenation component(s) in the catalyst suitably range from about 0.5% to about 10% by weight of Group VIII component(s) and from 5% to about 25% by weight of Group VI metal component(s), calculated as metal oxide(s) per 100 parts by weight of total catalyst, where the percentages by weight are based on the weight of the catalyst before sulfiding. The hydrogenation component(s) in the catalyst may be in the oxidic and/or sulfidic form.

Hydrogenation

SSZ-56 can be used in a catalyst to catalyze hydrogenation of a hydrocarbon feed containing unsaturated hydrocarbons. The unsaturated hydrocarbons can comprise olefins, dienes, polyenes, aromatic compounds and the like.

Hydrogenation is accomplished by contacting the hydrocarbon feed containing unsaturated hydrocarbons with hydrogen in the presence of a catalyst comprising SSZ-56. The catalyst can also contain one or more metals of Group VIB and Group VIII, including salts, complexes and solutions thereof. Reference to these catalytically active metals is intended to encompass such metals or metals in the elemental state or in some form such as an oxide, sulfide, halide, carboxylate and the like. Examples of such metals include metals, salts or complexes wherein the metal is selected from the group consisting of platinum, palladium, rhodium, iridium or combinations thereof, or the group consisting of nickel, molybdenum, cobalt, tungsten, titanium, chromium, vanadium, rhenium, manganese and combinations thereof.

The hydrogenation component of the catalyst (i.e., the aforementioned metal) is present in an amount effective to provide the hydrogenation function of the catalyst, preferably in the range of from 0.05 to 25% by weight.

Hydrogenation conditions, such as temperature, pressure, space velocities, contact time and the like are well known in the art.

EXAMPLES

The following examples demonstrate but do not limit the present invention.

Example 1

Synthesis of the directing agent
N,N-Diethyl-2-Methyidecahydroquinolinium
Hydroxide The parent amine 2-Methyldecahydroquinoline was obtained by hydrogenation of 2-methylquinoline (quinaldine) as described below. A 1000-ml stainless steel hydrogenation vessel was charged with 200 gm (1.4 mol) of 2-methylquinoline (quinaldine), purchased from Aldrich Chemical Company, and 300 ml glacial acetic acid, 10 gm of $PtO_2$ and 15 ml concentrated $H_2SO_4$. The mixture was purged twice with nitrogen (the vessel was pressurized with nitrogen to 1000 psi and evacuated). Then, the reaction vessel was pressurized to 1500-psi of hydrogen gas and allowed to stir at 50° C. overnight. The pressure dropped overnight and the vessel was pressurized back to 1500 psi (with $H_2$ gas) and let to stir until no further drop in the pressure was observed. Once the reaction was complete, the mixture was filtered and the filtrate was treated with 50 wt % aqueous sodium hydroxide solution until a pH of ~9 was achieved. The treated filtrate was diluted with 1000 ml diethyl ether. The organic layer was separated, washed with water and brine, and dried over anhydrous $MgSO_4$. Concentration under vacuum (using rotary evaporator) gave the amine as a pair of isomers (cis-fused and trans-fused ring system with the methyl group in the equatorial position in both isomers) in 97% yield (208 gm) in a ratio of 1.1:0.9 trans-fused:cis-fused. The authenticity of the product was established by spectral data analysis including NMR, IR and GCMS spectroscopy. In principle, there are four likely isomers, but only two isomers were produced.

N-Ethyl-2-methyldecahydroquinolinium hydroiodide was prepared according to the method described below. To a solution 100 gm (0.65 mol) of 2-methyldecahydroquinoline (trans and cis) in 350 ml acetonitrile, 111 gm (0.72 mole) of ethyl iodide was added. The mixture was stirred (using an overhead stirrer) at room temperature for 96 hours. Then, an additional ½ mole equivalent of ethyl iodide was added and the mixture was heated at reflux for 6 hours. The reaction mixture was concentrated on a rotary evaporator at reduced pressure and the obtained solids were rinsed with 500 ml ethyl ether to remove any unreactive amines and excess iodide. The reaction afforded a mixture of two N-ethyl-2-methyl-decahydroquinolinium hydroiodide salts (mono-ethyl derivatives) and a small mixture of the quaternized derivatives. The products were isolated by recrystallization from isopropyl alcohol several times to give the pure trans-fused ring N-ethyl-2-methyl-decahydroquinolinium hydroiodide and the pure cis-fused ring N-ethyl-2-methyl-decahydroquinolinium hydroiodide (see the scheme below).

N,N-Diethyl-2-methyldecahydroquinolinium iodide was prepared according to the procedure shown below. The procedure below is typical for making the N,N-diethyl-2-methyl-decahydro-quinolinium iodide. The obtained transfused ring N-ethyl-2-methyl-decahydroquinolinium hydroiodide (28 gm, 0.09 mol) was added to an acetonitrile (150 ml) and $KHCO_3$ (14 gm, 0.14 mol) solution. To this solution, 30 gm (0.19 mol) of ethyl iodide was added and the resulting mixture was stirred (with an overhead stirrer) at room temperature for 72 hours. Then, one more mole equivalent of ethyl iodide was added and the reaction was heated to reflux and allowed to stir at the reflux temperature for 6 hours. Heating was stopped and the reaction was allowed to further stir at room temperature overnight. The reaction was worked up by removing the excess ethyl iodide and the solvent at reduced pressure on a rotary evaporator. The resulting solids were suspended in 500 ml chloroform, which dissolves the desired product and leaves behind the unwanted $KHCO_3$ and its salt by-products. The solution was filtered, and the filtrate was dried over anhydrous $MgSO_4$. Filtration followed by concentration at reduced pressure on a rotary evaporator, gave the desired N,N-diethyl-2-methyl-decahydroquinolinium iodide as a pale tan-colored solid. The solid was further purified by recrystallization in isopropyl alcohol. The reaction afforded 26.8 gm (87% yield). The N,N-diethyl-2-methyl-decahydroquinolinium iodide of the cis-fused ring isomer was made according to the procedure described above. The trans-fused ring derivative A (see the scheme 1 below) is the templating agent (SDA) useful for making SSZ-56.

N,N-Diethyl-2-methyldecahydroquinolinium
hydroxide

The hydroxide version of N,N-diethyl-2-methyldecahydro-quinolinium cation was prepared by ion exchange as described in the procedure below. To a solution of 20 gm (0.06 mol) of N,N-diethyl-2-methyldecahydro-quinolinium iodide in 80 ml water, 80 gm of OH-ion exchange resin (BIO RAD® AGI-X8) was added, and the resulting mixture was allowed to gently stir at room temperature for few hours. The mixture was filtered and the ion exchange resin was rinsed with additional 30 ml water (to ensure removing all the cations from the resin). The rinse and the original filtrate were combined and titration analysis on a small sample of the filtrate with 0.1N HCl indicated a 0.5M OH ions concentration (0.055 mol cations). Scheme 1 below depicts the synthesis of the templating agent.

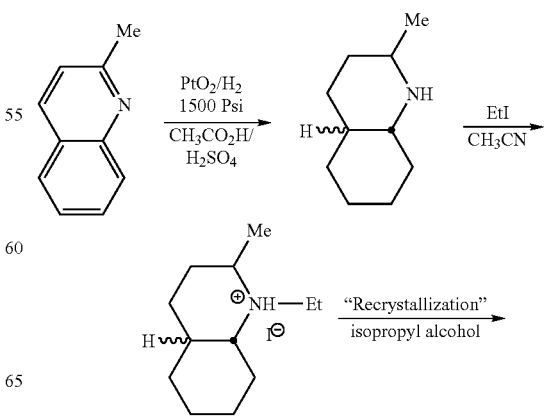

Scheme 1

-continued

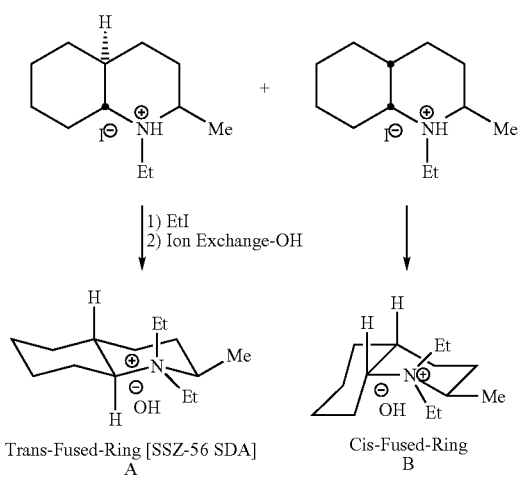

1) EtI
2) Ion Exchange-OH

Trans-Fused-Ring [SSZ-56 SDA]
A

Cis-Fused-Ring
B

There are 4 possible isomers (depicted below) from the synthesis, but only two isomers were produced: trans-fused-equatorial methyl A and cis-fused-equatorial methyl B.

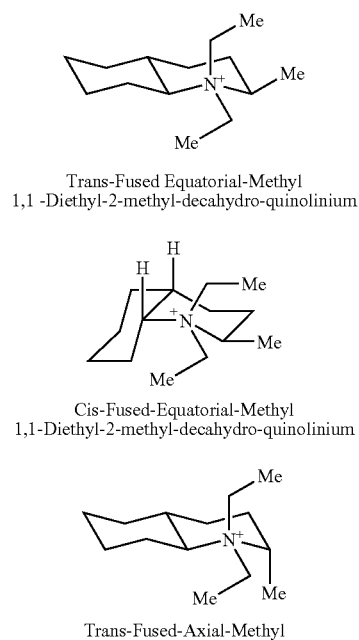

Trans-Fused Equatorial-Methyl
1,1-Diethyl-2-methyl-decahydro-quinolinium

Cis-Fused-Equatorial-Methyl
1,1-Diethyl-2-methyl-decahydro-quinolinium

Trans-Fused-Axial-Methyl
1,1-Diethyl-2-methyl-decahydro-quinolinium

Cis-Fused-Axial-Methyl
1,1-Diethyl-2-methyl-decahydro-quinolinium

A

B

C

D

Example 2

Synthesis of Borosilicate SSZ-56 from Calcined Boron-BETA Zeolite

In a 23 cc Teflon liner, 3 gm of 0.5M solution (1.5 mmol) of N,N-diethyl-2-methyldecahydroquinolinium hydroxide (the trans-fused ring isomer), 0.5 gm of 1.0N solution of aqueous NaOH (0.5 mmol), 4.5 gm of de-ionized water, and 0.65 gm of calcined boron-BETA zeolite were all mixed. The Teflon liner was capped and placed in a Parr reactor and heated in an oven at 150° C. while tumbling at about 43 rpm. The reaction progress was checked by monitoring the gel's pH and by looking for crystal formation using Scanning Electron Microscopy (SEM) at 3-6 days intervals. The reaction was usually completed after heating for 18-24 days (shorter crystallization periods were achieved at 160° C.). The final pH at the end of the reaction ranged from 10.8-11.6. Once the crystallization was completed (by SEM analysis), the reaction mixture (usually a white fine powdery precipitate with clear liquid) was filtered. The collected solids were rinsed a few times with de-ionized water (~1000 ml), and then let to air-dry overnight followed by drying in an oven at 120° C. for 15-20 minutes. The reaction yielded about 0.55-0.6 gm of pure boron-SSZ-56 as determined by XRD analysis.

Example 3

Seeded Preparation of Borosilicate SSZ-56

In a 23 cc Teflon liner, 3 gm of 0.5M solution (1.5 mmol) of N,N-diethyl-2-methyldecahydroquinolinium hydroxide (the trans-fused ring isomer), 0.5 gm of 1.0N solution of aqueous NaOH (0.5 mmol), 4.5 gm of de-ionized water, 0.65 gm of calcined boron-BETA zeolite and 0.03 gm of SSZ-56 (made as described above) were mixed. The Teflon liner was capped and placed in a Parr reactor and heated in an oven at 150° C. while tumbling at about 43 rpm. The reaction progress was checked by monitoring the gel's pH and by looking for crystal formation using Scanning Electron Microscopy (SEM) at 3 day intervals. The crystallization was complete (SEM analysis) after heating for 6 days. The final pH at the end of the reaction was usually 11.2. Once completed, the reaction mixture was filtered, and the collected solids were rinsed with de-ionized water (~1000 ml), and then let to air-dry overnight followed by drying in an oven at 120° C. for 15-20 minutes. The reaction yielded 0.6 gm of pure boron-SSZ-56. Identity and characterization of the material was determined by XRD analysis.

Example 4

Direct Synthesis of Borosilicate SSZ-56 from Sodium Borate Decahydrate as the Boron Sources and CAB-O-SIL M-5 as the Silicon Source In a 23 cc Teflon liner, 6 gm of 0.5M solution (3 mmol) of N,N-diethyl-2-methyldecahydroquinolinium hydroxide (the trans-fused ring isomer), 1.2 gm of 1.0N solution of aqueous NaOH (1.2 mmol), 4.8 gm of de-ionized water, and 0.065 gm of sodium borate decahydrate were mixed and stirred until the sodium borate was completely dissolved. Then, 0.9 gm of Cab-O—Sil M-5 (~98% SiO2) was added and thoroughly mixed. The resulting gel was capped and placed in a Parr reactor and heated in an oven at 160° C. while tumbling at about 43 rpm. The reaction progress was checked by monitoring the gel's pH and by looking for crystal formation using Scanning Electron Microscopy (SEM) at 6 days intervals. The reaction was usually completed after heating for 18-24 days. The final pH at the end of the reaction ranged from 11.5-12.3. Once the crystallization was completed (by SEM analysis), the reaction mixture, a white fine powdery precipitate with clear liquid, was filtered. The collected solids were rinsed few times with de-ionized water (~1000 ml), and then air-dried overnight followed by drying in an oven at 120° C. for 15 minutes. The reaction usually yields about 0.75-0.9 gm of pure boron-SSZ-56.

Example 5

Seeded Synthesis of Borosilicate SSZ-56 from Sodium Borate Decahydrate as the Boron Source and CAB-O-SIL M-5 as the Silicon Source In a 23 cc Teflon liner, 6 gm of 0.5M solution (3 mmol) of N,N-diethyl-2-methyldecahydroquinolinium hydroxide (the trans-fused ring isomer), 1.2 gm of 1.0N solution of aqueous NaOH (1.2 mmol), 4.8 gm of de-ionized water, and 0.062 gm of sodium borate decahydrate were mixed and stirred until the sodium borate was completely dissolved. Then, 0.9 gm of Cab-O-Sil M-5 (~98% SiO2) and 0.04 gm of B-SSZ-56 made as in Example 4 were added and thoroughly mixed. The resulting gel was capped and placed in a Parr reactor and heated in an oven at 160° C. while tumbling at about 43 rpm. The reaction progress was checked by monitoring the gel's pH and by looking for crystal formation using Scanning Electron Microscopy (SEM) at 3-5 days intervals. The reaction was completed after heating for 7 days. The final pH at the end of the reaction was about 12.2. Once the crystallization was completed (by SEM analysis), the reaction mixture, a white fine powdery precipitate with clear liquid, was filtered. The collected solids were rinsed few times with de-ionized water (~1000 ml), and then air-dried overnight followed by drying in an oven at 120° C. for 15 minutes. The reaction yielded 0.88 gm of pure boron-SSZ-56.

Example 6

Calcination of SSZ-56

Removing the templating agent molecules (structure-directing agents: SDAs) from zeolite SSZ-56 to free its channels and cavities was accomplished by the calcination method described below. A sample of the as-made SSZ-56 synthesized according to the procedures of Examples 2, 3, 4 or 5 discussed above is calcined by preparing a thin bed of SSZ-56 in a calcination dish which was heated in a muffle furnace from room temperature to 595° C. in three stages. The sample was heated to 120° C. at a rate of 1° C./minute and held for 2 hours. Then, the temperature was ramped up to 540° C. at a rate of 1° C./minute and held for 5 hours. The temperature was then ramped up again at 1° C./minute to 595° C. and held there for 5 hours. A nitrogen stream with a slight bleed of air was passed over the zeolite at a rate of 20 standard cubic feet (0.57 standard cubic meters) per minute during heating the calcination process.

Example 7

Ammonium-Ion Exchange of SSZ-56

The Na$^+$ form of SSZ-56 prepared as in Examples 2, 3, 4 or 5 and calcined as in Example 6 was converted to NH$_4^+$-SSZ-56 form by heating the material in an aqueous solution of NH$_4$NO$_3$ (typically 1 gm NH$_4$NO$_3$/1 gm SSZ-56 in 20 ml H$_2$O) at 90° C. for 2-3 hours. The mixture was then filtered and the step was repeated as many times as desired (usually done 2-3 times). After filtration, the obtained NH$_4$-exchanged-product was washed with de-ionized water and air dried. The NH$_4^+$ form of SSZ-56 can be converted to the H$^+$ form by calcination to 540° C. (as described in Example 6 above stopping at the end of the second stage).

Example 8

Preparation of Aluminosilicate SSZ-56 by Aluminum Exchange of Boron-SSZ-56

The aluminosilicate version of SSZ-56 was prepared by way of exchanging borosilicate SSZ-56 with aluminum nitrate according to the procedure described below. The H$^+$ version of calcined borosilicate SSZ-56 (prepared as in Examples 2, 3, 4 or 5 and treated with ammonium nitrate and calcined as Example 6) was easily converted to the aluminosilicate SSZ-56 by suspending the zeolite (H$^+$/borosilicate SSZ-56) in 1M solution of aluminum nitrate nonahydrate (10 ml of 1M Al(NO$_3$)$_3$.9H$_2$O soln./1 gm SSZ-56). The suspension was heated at reflux overnight. The resulting mixture was then filtered and the collected solids were thoroughly rinsed with de-ionized water and air-dried overnight. The solids were further dried in an oven at 120° C. for 2 hours. The exchange can also be done on the Na$^+$ version of SSZ-56 (as prepared in Examples 2, 3, 4 or 5 and calcined as in Example 6).

Example 9

Nitrogen Adsorption (MicroPore Volume Analysis)

The Na$^+$ and H$^+$ forms of SSZ-56 as synthesized in Examples 2 and 4 above and treated as in Examples 6 and 7 was subjected to a surface area and micropore volume analysis using N$_2$ as adsorbate and via the BET method. The zeolite exhibited a considerable void volume with a micropore volume of 0.18 cc/g for Na$^+$ form, and 0.19 cc/gm for the H$^+$ form.

Example 10

Argon Adsorption (MicroPore Volume Analysis)

A calcined sample of Na$^+$ version of borosilicate SSZ-56 (synthesized as in Example 2 and calcined as in Example 6) had a micropore volume of 0.16 cc/gm based on argon adsorption isotherm at 87.50° K (−186° C.) recorded on ASAP 2010 equipment from Micromerities. The sample was first degassed at 400° C. for 16 hours prior to argon adsorption. The low-pressure dose was 2.00 cm3/g (STP). A maximum of one hour equilibration time per dose was used and the total run time was 37 hours. The argon adsorption isotherm was analyzed using the density function theory (DFT) formalism and parameters developed for activated carbon slits by Olivier (Porous Mater. 1995, 2, 9) using the Saito Foley adaptation of the Horvarth-Kawazoe formalism (Microporous Materials, 1995, 3, 531) and the conventional t-plot method (J. Catalysis, 1965, 4, 319).

Example 11

Constraint Index Test

The hydrogen form of SSZ-56 synthesized as in Example 2 was calcined and ammonium exchanged as in Examples 6 and 7 was aluminum exchanged as in Example 8. The obtained aluminum-exchanged sample of SSZ-56 was then ammonium exchanged as in Example 7 followed by calcination to 540° C. as in Example 6. The H-Al-SSZ-56 was pelletized at 4 KPSI, crushed and granulated to 20-40 mesh. A 0.6 gram sample of the granulated material was calcined in air at 540° C. for 4 hours and cooled in a desiccator to ensure dryness. Then, 0.5 gram was packed into a ⅜ inch stainless steel tube with alundum on both sides of the molecular sieve bed. A Lindburg furnace was used to heat the reactor tube. Helium was introduced into the reactor tube at 10 cc/min. and at atmospheric pressure. The reactor was heated to about 315° C., and a 50/50 feed of n-hexane and 3-methylpentane is introduced into the reactor at a rate of 8 µl/min. The feed was delivered by a Brownlee pump. Direct sampling into a GC began after 10 minutes of feed introduction. The Constraint Index (CI) value was calculated from the GC data using methods known in the art. SSZ-56 had a CI of 0.76 and a conversion of 79% after 15 minutes on stream. The material fouled rapidly and at 105 minutes the CI was 0.35 and the conversion was 25.2%. The CI test showed the material was very active catalytic material.

Example 12 n-Hexadecane Hydrocracking Test

A 1 gm sample of SSZ-56 (prepared as described for the Constraint Index test in Example 11) was suspended in 10 gm de-ionized water. To this suspension, a solution of $Pd(NH_3)_4(NO_3)_2$ at a concentration which would provide 0.5 wt. % Pd with respect to the dry weight of the molecular sieve sample was added. The pH of the solution was adjusted to pH of 9.2 by a drop-wise addition of 0.15N solution of ammonium hydroxide. The mixture was then heated in an oven at 75° C. for 48 hours. The mixture was then filtered through a glass frit, washed with de-ionized water, and air-dried. The collected Pd-SSZ-56 sample was slowly calcined up to 482° C. in air and held there for three hours.

The calcined Pd/SSZ-56 catalyst was pelletized in a Carver Press and granulated to yield particles with a 20/40 mesh size. Sized catalyst (0.5 g) was packed into a ¼ inch OD tubing reactor in a micro unit for n-hexadecane hydroconversion. The table below gives the run conditions and the products data for the hydrocracking test on n-hexadecane.

As the results show in the table below, SSZ-56 is a very active and isomerisation selective catalyst at 96.5% n-$C_{16}$ conversion at 256° C.

| | |
|---|---|
| Temperature | 256° C. (496° F.) |
| Time-on-Stream (hrs.) | 71.4-72.9 |
| WHSV | 1.55 |
| PSIG | 1200 |
| Titrated? | NO |
| n-16, % Conversion | 96.5 |
| Hydrocracking Conv. | 35.2 |
| Isomerization Selectivity, % | 63.5 |
| Cracking Selectivity, % | 36.5 |
| $C_{4-}$ % | 2.3 |
| $C_5/C_4$ | 15.2 |
| $C_{5+}C_6/C_5$, % | 19.3 |
| DMB/MP | 0.05 |
| $C_4$-$C_{13}$ i/n | 3.7 |
| $C_7$-$C_{13}$ yield | 27.7 |

What is claimed is:

1. A process for converting hydrocarbons comprising contacting a hydrocarbonaceous feed at hydrocarbon converting conditions with a catalyst comprising a molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table 2.

2. The process of claim 1 wherein the molecular sieve is predominantly in the hydrogen form.

3. The process of claim 1 wherein the molecular sieve is substantially free of acidity.

4. The process of claim 1 wherein the process is a hydrocracking process comprising contacting the catalyst with a hydrocarbon feedstock under hydrocracking conditions.

5. The process of claim 4 wherein the molecular sieve is predominantly in the hydrogen form.

6. The process of claim 1 wherein the process is a dewaxing process comprising contacting the catalyst with a hydrocarbon feedstock under dewaxing conditions.

7. The process of claim 6 wherein the molecular sieve is predominantly in the hydrogen form.

8. The process of claim 1 wherein the process is a process for improving the viscosity index of a dewaxed product of waxy hydrocarbon feeds comprising contacting the catalyst with a waxy hydrocarbon feed under isomerization dewaxing conditions.

9. The process of claim 8 wherein the molecular sieve is predominantly in the hydrogen form.

10. The process of claim 1 wherein the process is a process for producing a $C_{20+}$ lube oil from a $C_{20+}$ olefin feed comprising isomerizing said olefin feed under isomerization conditions over the catalyst.

11. The process of claim 10 wherein the molecular sieve is predominantly in the hydrogen form.

12. The process of claim 10 wherein the catalyst further comprises at least one Group VIII metal.

13. The process of claim 1 wherein the process is a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15-3000 psi (0.103-20.7 MPa) under dewaxing conditions with the catalyst.

14. The process of claim 13 wherein the molecular sieve is predominantly in the hydrogen form.

15. The process of claim 13 wherein the catalyst further comprises at least one Group VIII metal.

16. The process of claim 13 wherein said catalyst comprises a layered catalyst comprising a first layer comprising the molecular sieve and at least one Group VIII metal, and a second layer comprising an aluminosilicate zeolite which is more shape selective than the molecular sieve of said first layer.

17. The process of claim 1 wherein the process is a process for preparing a lubricating oil which comprises:

hydrocracking in a hydrocracking zone a hydrocarbonaceous feedstock to obtain an effluent comprising a hydrocracked oil; and catalytically dewaxing said effluent comprising hydrocracked oil at a temperature of at least about 400° F. (204° C.) and at a pressure of from about 15 psig to about 3000 psig (0.103 to 20.7 MPa gauge) in the presence of added hydrogen gas with the catalyst.

18. The process of claim 17 wherein the molecular sieve is predominantly in the hydrogen form.

19. The process of claim 17 wherein the catalyst further comprises at least one Group VIII metal.

20. The process of claim 1 wherein the process is a process for isomerization dewaxing a raffinate comprising contacting said raffinate in the presence of added hydrogen under isomerization dewaxing conditions with the catalyst.

21. The process of claim 20 wherein the molecular sieve is predominantly in the hydrogen form.

22. The process of claim 20 wherein the catalyst further comprises at least one Group VIII metal.

23. The process of claim 20 wherein the raffinate is bright stock.

24. The process of claim 1 wherein the process is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C. under aromatic conversion conditions with the catalyst.

25. The process of claim 24 wherein the molecular sieve is substantially free of acid.

26. The process of claim 24 wherein the molecular sieve contains a Group VIII metal component.

27. The process of claim 1 wherein the process is a catalytic cracking process comprising contacting a hydrocarbon feedstock in a reaction zone under catalytic cracking conditions in the absence of added hydrogen with the catalyst.

28. The process of claim 27 wherein the molecular sieve is predominantly in the hydrogen form.

29. The process of claim 27 wherein the catalyst additionally comprises a large pore crystalline cracking component.

30. The process of claim 1 wherein the process is an isomerization process for isomerizing $C_4$ to $C_7$ hydrocarbons, comprising contacting a feed having normal and slightly branched $C_4$ to $C_7$ hydrocarbons under isomerizing conditions with the catalyst.

31. The process of claim 30 wherein the molecular sieve is predominantly in the hydrogen form.

32. The process of claim 30 wherein the molecular sieve has been impregnated with at least one Group VIII metal.

33. The process of claim 30 wherein the catalyst has been calcined in a steam/air mixture at an elevated temperature after impregnation of the Group VIII metal.

34. The process of claim 32 wherein the Group VIII metal is platinum.

35. The process of claim 1 wherein the process is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of the catalyst.

36. The process of claim 35 wherein the molecular sieve is predominantly in the hydrogen form.

37. The process of claim 35 wherein the olefin is a $C_2$ to $C_4$ olefin.

38. The process of claim 37 wherein the aromatic hydrocarbon and olefin are present in a molar ratio of about 4:1 to about 20:1, respectively.

39. The process of claim 37 wherein the aromatic hydrocarbon is selected from the group consisting of benzene, toluene, ethylbenzene, xylene, naphthalene, naphthalene derivatives, dimethylnaphthalene or mixtures thereof.

40. The process of claim 1 wherein the process is a process for transalkylating an aromatic hydrocarbon which comprises contacting under transalkylating conditions an aromatic hydrocarbon with a polyalkyl aromatic hydrocarbon under at least partial liquid phase conditions and in the presence of the catalyst.

41. The process of claim 40 wherein the molecular sieve is predominantly in the hydrogen form.

42. The process of claim 40 wherein the aromatic hydrocarbon and the polyalkyl aromatic hydrocarbon are present in a molar ratio of from about 1:1 to about 25:1, respectively.

43. The process of claim 40 wherein the aromatic hydrocarbon is selected from the group consisting of benzene, toluene, ethylbenzene, xylene, or mixtures thereof.

44. The process of claim 40 wherein the polyalkyl aromatic hydrocarbon is a dialkylbenzene.

45. The process of claim 1 wherein the process is a process to convert paraffins to aromatics which comprises contacting paraffins under conditions which cause paraffins to convert to aromatics with a catalyst comprising the molecular sieve and gallium, zinc, or a compound of gallium or zinc.

46. The process of claim 1 wherein the process is a process for isomerizing olefins comprising contacting said olefin under conditions which cause isomerization of the olefin with the catalyst.

47. The process of claim 1 wherein the process is a process for isomerizing an isomerization feed comprising an aromatic $C_8$ stream of xylene isomers or mixtures of xylene isomers and ethylbenzene, wherein a more nearly equilibrium ratio of ortho-, meta and para-xylenes is obtained, said process comprising contacting said feed under isomerization conditions with the catalyst.

48. The process of claim 1 wherein the process is a process for oligomerizing olefins comprising contacting an olefin feed under oligomerization conditions with the catalyst.

49. A process for converting oxygenated hydrocarbons comprising contacting said oxygenated hydrocarbon under conditions to produce liquid products with a catalyst comprising a molecular sieve having a mole ratio greater than about 15 of an oxide of a first tetravalent element to an oxide of a second tetravalent element which is different from said first tetravalent element, trivalent element, pentavalent element or mixture thereof and having, after calcination, the X-ray diffraction lines of Table 2.

50. The process of claim 49 wherein the oxygenated hydrocarbon is a lower alcohol.

51. The process of claim 50 wherein the lower alcohol is methanol.

52. The process of claim 1 wherein the process is a process for the production of higher molecular weight hydrocarbons from lower molecular weight hydrocarbons comprising the steps of:

(a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and (b) withdrawing from said reaction zone a higher molecular weight hydrocarbon-containing stream.

53. The process of claim 52 wherein the metal or metal compound comprises a lanthanide or actinide metal or metal compound.

54. The process of claim 52 wherein the lower molecular weight hydrocarbon is methane.

55. The process of claim 1 wherein the process is a process for polymerizing 1-olefins, which process comprises contacting 1-olefin monomer with a catalytically effective amount of a catalyst composition comprising
   (A) a molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table 2; and
   (B) an organotitanium or organochromium compound under polymerization conditions which include a temperature and pressure suitable for initiating and promoting the polymerization reaction.

56. The process of claim 55 wherein oxide (1) is silicon oxide, and oxide (2) is an oxide selected from aluminum oxide, gallium oxide, iron oxide, boron oxide, titanium oxide, indium oxide.

57. The process of claim 55 wherein the 1-olefin monomer is ethylene.

58. The process of claim 56 wherein the 1-olefin monomer is ethylene.

59. The process of claim 1 wherein the process is a process for hydrogenating a hydrocarbon feed containing unsaturated hydrocarbons, the process comprising contacting the feed with hydrogen under conditions which cause hydrogenation with the catalyst.

60. The process of claim 59 wherein the catalyst contains metals, salts or complexes wherein the metal is selected from the group consisting of platinum, palladium, rhodium, iridium or combinations thereof, or the group consisting of nickel, molybdenum, cobalt, tungsten, titanium, chromium, vanadium, rhenium, manganese and combinations thereof.

61. A process for hydrotreating a hydrocarbon feedstock comprising contacting the feedstock with a hydrotreating catalyst and hydrogen under hydrotreating conditions, wherein the catalyst comprises a molecular sieve having a mole ratio greater than about 15 of (1) an oxide of a first tetravalent element to (2) an oxide of a trivalent element, pentavalent element, second tetravalent element which is different from said first tetravalent element or mixture thereof and having, after calcination, the X-ray diffraction lines of Table 2.

62. The process of claim 61 wherein the catalyst contains a Group VIII metal or compound, a Group VI metal or compound or combinations thereof.

63. A process for hydrotreating a hydrocarbon feedstock comprising contacting the feedstock with a hydrotreating catalyst and hydrogen under hydrotreating conditions, wherein the catalyst comprises a molecular sieve having a mole ratio greater than about 15 of (1) an silicon oxide (2) an oxide selected from aluminum oxide, gallium oxide, iron oxide, boron oxide, titanium oxide, indium oxide and mixtures thereof, and having, after calcination, the X-ray diffraction lines of Table 2.

64. The process of claim 63 wherein the oxides comprise silicon oxide and aluminum oxide.

65. The process of claim 63 wherein the oxides comprise silicon oxide and boron oxide.

66. The process of claim 63 wherein the oxide comprises silicon oxide.

67. The process of claim 63 wherein the catalyst contains a Group VIII metal or compound, a Group VI metal or compound or combinations thereof.

68. A process for converting hydrocarbons comprising contacting a hydrocarbonaceous feed at hydrocarbon converting conditions with a catalyst comprising a molecular sieve having a mole ratio greater than about 15 of (1) silicon oxide to (2) an oxide selected from aluminum oxide, gallium oxide, iron oxide, boron oxide, titanium oxide, indium oxide and mixtures thereof, and having, after calcination, the X-ray diffraction lines of Table 2.

* * * * *